United States Patent
Marellapudi et al.

(12) 
(10) Patent No.: US 6,403,344 B1
(45) Date of Patent: Jun. 11, 2002

(54) ENZYMATIC PROCESS FOR THE PREPARATION OF AN ACETYLATED PHOSPHOLIPID

(75) Inventors: Sri Lakshmi Karuna Marellapudi; Vandana Vemulapalli; Vijayalakshmi Penumarthy; Badari Narayana Prasad Rachapudi, all of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/820,191

(22) Filed: Mar. 28, 2001

(51) Int. Cl.[7] .............................. C12P 9/00; C12P 13/00; C12N 9/18; C12N 9/20
(52) U.S. Cl. ........................ 435/131; 435/128; 435/197; 435/198
(58) Field of Search ................................. 435/131, 197, 435/198, 128

(56) References Cited

U.S. PATENT DOCUMENTS 5,902,738 A * 5/1999 Orsat et al. .................. 435/155

OTHER PUBLICATIONS

Computer Abstract "Contents and Abstracts of Latest BBB" Laumen et al. vol. 63, No. 8 1999.*

* cited by examiner

*Primary Examiner*—Herbert J. Lilling
(74) *Attorney, Agent, or Firm*—Ladas & Parry

(57) ABSTRACT

The present invention provides an enzymatic process for the preparation of an acetylated phospholipid from a lecithin by acetylating the lecithin in the presence of vinyl acetate and a catalyst comprising lipase from *Mucor miehei* having 1,3-position specificity, separating the desired acetylated phospholipid.

14 Claims, No Drawings

ENZYMATIC PROCESS FOR THE PREPARATION OF AN ACETYLATED PHOSPHOLIPID

FIELD OF THE INVENTION

The present invention relates to an enzymatic process for the preparation of an acetylated phospholipid. The invention particularly relates to an enzymatic process for the preparation of an acetylated phospholipid from vegetable lecithins such as soybean lecithin, rapeseed lecithin etc., and animal lecithins like egg yolk lecithin or pure phosphatidylethanolamine isolated from the above lecithins. The commercial lecithins or phosphatidylethanolamine are acetylated by using vinyl acetate as acylating agent in presence of lipase from *Mucor miehei* having 1,3-position specificity as catalyst.

BACKGROUND OF THE INVENTION

Commercial lecithin is an important co-product of oil processing obtained during degumming step. For example, soybean lecithin is a complex mixture and comprises of phospholipids and triglycerides, with minor amounts of other constituents like phytoglycolipids, phytosterols, tocopherols and fatty acids. The major phospholipids present in vegetable lecithins are phosphatidylcholine, phosphatidylethanolamine and phosphatidylinositol. The egg yolk lecithin contains phosphatidylcholine and phosphatidylethanolamine as major phospholipids. Lecithin has potential as a multifunctional additive for food, pharmaceutical and industrial applications. The primary usage of lecithin in food is as an emulsifier. (Dashiell, G. L., in Lecithins: Sources, Manufacture and Uses, edited by B. F. Szuhaj, American Oil Chemical Society, Champaign Ill., 1989, p. 213). Acetylated lecithin exhibits improved fluid properties, improved water dispersability, and is effective oil-in-water emulsifiers for a wide variety of food formulations. (J. S. Schmidt and F. T. Orthoefer in Lecithins, B. F. Szuhaj and G. R. List eds., American Oil Chemists'Society, Champaign, Ill., 1985. p.183–212). Acetylation occurs primarily on the amino group of phosphatidylethanolamine. Moderately and highly acetylated lecithins are resistant to heat and can be repeatedly heated and cooled without darkening. The intended uses of minimally acetylated products are in infant foods coffee whiteners, meat sauces and gravies, and for oil-in-water cosmetic emulsions. Moderately and maximally acetylated products are used in cheese sauces, shortenings, and as release agents in pumpable and aerosol formulations, (Bailey's Industrial Oil and Fat Products, edited by Y. H. Hvi, Vol 1, $5^{th}$ Ed., John Wiley & Sons, N.Y., 1966, p.341).

There have been sporadic attempts to prepare acetylated lecithin from soybean lecithin. Unilever [Netherlands Patent 6,700,366 (1967)] prepared acetylated lecithin by react soya lecithin (100 g) containing 65% phosphatides with 2 g of acetic anhydride at 70° C. The mixture was stirred for 25 minutes and the acetic acid was distilled at 3 mm yielding 101 g of a mixture containing acetylated lecithin. Central Soya Company Inc., [U.S. Pat. No. 3,301,881 (1967)] in their studies used carboxylic acid anhydride like acetic anhydride for the acetylation of phospholipids from vegetable lecithins. J. Eichberg [U.S. Pat. No. 3,359,201 (1967)] also reported a similar methodology to prepare acetylated lecithin using acetic anhydride as acylating agent. According to R. Aneja and J. S. Chadha [Fett Seifen 73, 643–651 (1971)] acetylation was incomplete with acetic anhydride even after prolonged periods under reflux. However, in the presence of tertiary amine, the reaction was rapid and essentially complete in a few minutes at room temperature. Accordingly, Aneja, R. [U.S. Pat. No. 3,704,254 (1972)] used similar methodology by stirring soybean lecithin (100 g) and acetic anhydride (4 g) together vigorously under nitrogen at 74° C for 2 hr followed by tertiary amine treatment. The water dispersability of soybean lecithin was improved by acetylation with acetic anhydride at 170° F. followed by hydroxylation with 35% hydrogen peroxide [U.S. Pat. No. 3,962,292 (1976)] and the product was dried and deodorized at 185–190° F. and 28 mm Hg vacuum. Crude soybean phosphatide (1 kg) was dried and dissolved in 4 liters of dichloromethane and mixed with 230 ml acetic acid and 200 g freshly calcinated basic aluminium oxide and refluxed for 4 hours. About half of the phosphatidylethanolamine was acetylated. The aluminium oxide was filtered and the solvent and excess acetic acid were removed under vacuum [Ger Pat. 2,615,120 (1977)]. Guenther, B. R. also prepared acetylated lecithin [Eur. Pat. 54,768 (1982) and U.S. Pat. No. 4,443,378 (1984)] by reacting 400 g of soybean phosphatide with 24 g of acetic anhydride at 50° C. for 1 hr. Soya lecithin was acylated with oleoyl chloride and triethylamine in 96% yield. N-Acyl phosphatidylethanolamine is useful as antioxidant for unsaturated fatty acids [Ger Pat. 4,141,842 (1993)]. Dashiell, G. L. and William E., (U.S. Pat. No. 4,479,977 (1984) prepared acetylated lecithin by treating lecithin with 2–5% of acetic anhydride and claims that the lecithin-based release agents with superior resistance to darkening, reduced production of objectionable odors, and retention of chemical integrity are produced (release agent for diverse applications). Liposome dispersions are prepared from acylated phospholipids in which the amino group of cephalin was monoacylated with a dicarboxylic acid. [U.S. Pat. No. 4,983,397 (1991)]. Phosphatidylethanolamine was reacted with dodecaniedioic acid in dry dichloromethane in presence of dicyclohexylcarbodiimide, triethylamine and absolute methanol and the mixture was incubated for 24 hours at 40° C. [U.S. Pat. No. 5,064,817 (1991)] to study the Phospholipase $A_2$ inhibitor activity.

Thus many of the processes reported used only acetic anhydride as acylating agent. Some processes involve the use of acetic anhydride/carboxylic acid anhydride as the acylating agent and triethylamine as catalyst. In another method acetic acid as acylating agent and calcinated basic aluminium oxide as catalyst were used. The conversion of phosphatidylethanolamine to N-acetyl phosphatidylethanolamine remains incomplete when only acetic anhydride is used for the reaction [R. A. Aneja, J. S. Chadha, J. A. knaggs, Biochim. Biophys. Res. Commun 36, 401 (1969)].]. However, R. Aneja and J. S. Chadha [Fett Seifen Anstrichmittel 73, 643–651 (1971)] reported that the reaction was rapid in the presence of tertiary amine as catalyst. Another disadvantage of chemical acetylation is O-acetylation reaction of free hydroxyl groups of phosphatidylinositol present in lecithin in addition to N-acetylation of phosphatidylethanolamine [R. Aneja and J. S. Chadha, Fett Seifen Anstrichmittel 73, 643–651 (1971)]. In general, chemical methods suffer several drawbacks such as low yields, and decomposition products that result in dark colored reaction products.

OBJECTS OF THE INVENTION

The main object of the present invention is to provide an enzymatic process for the first time for the preparation of acetylated phospholipids from vegetable lecithins such as soybean lecithin, rapeseed lecithin etc., and animal lecithins like egg yolk lecithin or pure phosphatidylethanolamine isolated from the above lecithins which obviates the drawbacks of the processes described above.

Another object of the present invention is to develop a simple method to use vinyl acetate as acylating agent, which can be used as a solvent also.

Yet another object of the present invention is to provide an enzymatic method using lipase from *Mucor miehei* having 1,3-position specificity, which can be carried out under mild conditions compared to existing chemical methodologies and which is also an eco-friendly process.

Yet another object of the present, invention is to acetylate amino group of phosphatidylethanolamine selectively without acetylation of hydroxyl group of phosphatidylinositol present in lecithin. This is possible only in the enzymatic acetylation using 1,3-specific lipase as described in the present invention. 1,3-Specific lipase does not allow the secondary hydroxyl group of phosphatidylinositol to participate in the reaction.

Yet another object of the present invention is to develop a simple enzymatic and economically cheaper method where the unreacted acylating reagent and the enzyme can be reused in the next batch of the reaction.

SUMMARY OF THE INVENTION

Accordingly, the present invention provides an enzymatic process for the preparation of an acetylated phospholipid from a lecithin, said process comprising acetylating the said lecithin in the presence of vinyl acetate and a catalyst comprising lipase from *Mucor miehei* having 1,3-position specificity, separating the desired acetylated phospholipid.

In one embodiment of the invention, the lecithin is selected from vegetable lecithins and animal lecithins.

In a further embodiment of the invention, the vegetable lecithin is selected from the group consisting of soybean lecithin and rapeseed lecithin.

In a further embodiment of the invention, the animal lecithin used comprises egg yolk lecithin.

In another embodiment of the invention, pure phosphatidylethanolamine is first isolated from the said lecithin, using vinyl acetate as an acylating agent in presence of said catalyst and then converted to the desired acetylated phospholipid.

In a further embodiment of the invention, the acetylating agent used selectively acetylates amino group of phosphatidylethanolamine without acetylation of hydroxyl group of phosphatidylinositol present in lecithin.

In another embodiment of the invention, the acylating agent and the enzyme catalyst are recycled for use in the next batch.

In another embodiment of the invention vinyl acetate is used in the range of 0.5 to 5 times volume of vinyl acetate based on the weight of lecithin/phosphatidylethanolamine.

In another embodiment of the invention, the ratio of weight of lecithin or phosphatidylethanolamine to lipase is in the range of 20:1 to 10:1.

In a further embodiment of the invention, the amount of the lipase enzyme preferably comprises 5 to 10 weight percent based on lecithin/phosphatidylethanolamine.

In another embodiment of the invention, the temperature of the reaction is in the range of 65–75° C., preferably in the range of 70–75° C.

In a further embodiment of the invention, the reaction time is in the range of 3 to 11 hours, preferably in the range of 3 to 8 hours.

DETAILED DESCRIPTION OF THE INVENTION

In the present invention a simple enzymatic method is carried out for the first time for the preparation of acetylated phospholipids from vegetable lecithins such as soybean lecithin, rapeseed lecithin etc., and animal lecithins like egg yolk lecithin or pure phosphatidylethanolamine isolated from the above lecithins by using vinyl acetate as acylating agent and lipase from *Mucor miehei* having 1,3-position specificity as catalyst.

The acylating agent vinyl acetate functions as the solvent as well. The amino group of phosphatidylethanolamine is selectively acetylated without acetylating of hydroxyl group of phosphatidylinositol present in lecithin. This is possible only in the enzymatic acetylation using 1,3-specific lipase as described in the present invention. 1,3-specific lipase does not allow the secondary hydroxyl group of phosphatidylinositol to participate in the reaction. The unreacted acylating reagent and the enzyme catalyst can be reused in the next batch of the reaction.

The broad applicability of the invention was examined by reacting the lecithins or phosphatidylethanolamine with vinyl acetate in presence of lipase from *Mucor miehei* having 1,3-position specificity to get acetylated phospholipids. The acetylation of lecithins or phosphatidylethanolamine is carried out with vinyl acetate. Preferably there is employed 0.5 to 5 times volume of vinyl acetate based on the weight of lecithin/phosphatidylethanolamine, more preferably 2 volumes of vinyl acetate.

The reaction is carried out using lipase from *Mucor miehei* having 1,3-position specificity. The amount of the lipase enzyme preferably comprises 5 to 10 weight percent based on lecithin/phosphatidylethanolamine, more preferably 5 weight percent of lypozyme.

The temperature of the reaction is generally in the range of 65–75° C., more preferably 70–75° C. Preferably there is employed a reaction time of 3 to 11 hours, more preferably 3 to 8 hours.

The following examples are given by way of illustration of the process of the invention and therefore should not be construed to limit the scope of the present invention. It must be understood that variations of the process exemplified below are possible without exceeding the scope of the invention.

EXAMPLE 1

Crude soybean lecithin (10 g) containing 50% phospholipids was taken in 50 ml of vinyl acetate and lipase from *Mucor miehei* (10% of lecithin, 1 g) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 10 hours of the reaction, the enzyme was filtered off and the excess of vinyl acetate was distilled out to obtain acetylated lecithin. The final yield of the product was 10.1 g.

EXAMPLE 2

Crude soybean lecithin (10 g) containing 50% phospholipids was taken in 50 ml of vinyl acetate and lipase from *Mucor miehei* (10% of lecithin, 1 g) was added to the contents, The reaction was carried out at 70–75° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 8 hours of the reaction the enzyme was filtered off and the excess of vinyl acetate was distilled out to obtain acetylated lecithin. The final yield of the product was 10.1 g.

EXAMPLE 3

Crude soybean lecithin (10 g) containing 50% of phospholipids was taken in 50 ml of vinyl acetate and lipase from *Mucor miehei* (5% of lecithin, 0.5 g) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 10 hours of the reaction the enzyme was filtered off and the excess of vinyl acetate was distilled out to obtain acetylated lecithin. The final yield of the product was 10.1 g.

EXAMPLE 4

Crude soybean lecithin (10 g) containing 50% of phospholipids was taken in 20 ml of vinyl acetate and lipase from *Mucor miehei* (5% of lecithin, 0.5 g) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 10 hours of the reaction the enzyme was filtered off and the excess of vinyl acetate was distilled out to obtain acetylated lecithin. The final yield of the product was 10.1 g.

EXAMPLE 5

Crude soybean lecithin (10 g) containing 50% phospholipids was taken in 50 ml of vinyl acetate and lipase from *Mucor miehei* (5% of lecithin, 5 g) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine wit ninhydrin spray indicated the completion of acetylation. After 10 hours of the reaction the enzyme was filtered off and the excess of vinyl acetate was distilled out to obtain acetylated lecithin. The final yield of the product was 100.7 g.

EXAMPLE 6

Crude rapeseed lecithin (10 g) containing 55% phospholipids was taken in 50 ml of vinyl acetate and lipase from *Mucor miehei* (10% of lecithin, 1.0 g) was added to the contents. The reaction was carried out at 65–70° C. by stirring the contents magnetically. The acetylation reaction was monitored by thin layer chromatography using chloroform: methanol:water (65:25:4, v/v/v) as solvent system. The disappearance of pink color spot of phosphatidylethanolamine with ninhydrin spray indicated the completion of acetylation. After 10 hours of the reaction, the enzyme was filtered off and the excess of vinyl acetate was distilled out to obtain acetylated lecithin. The final yield of the product was 10.1 g.

EXAMPLE 7

Crude egg yolk lecithin (10 g) containing 90% phospholipids was taken in 50 ml of vinyl acetate and lipase from *Mucor miehei* (10% of lecithin, 1.0 g) was added to the contents. The reaction was carried out at 65–70° C. by stirring the contents magnetically. The acetylation reaction was monitored by thin layer chromatography using chloroform: methanol:water (65:25:4, v/v/v) as solvent system. The disappearance of pink color spot of phosphatidylethanolamine with ninhydrin spray indicated the completion of acetylation. After 8 hours of the reaction, the enzyme was filtered off and the excess of vinyl acetate was distilled out to obtain acetylated lecithin. The final yield of the product was 10.2 g.

EXAMPLE 8

Pure phosphatidylethanolamine (0.5 g) isolated from soybean lecithin by silicic acid column chromatography was taken in 2.5 ml of vinyl acetate and lipase from *Mucor miehei* (10% of lecithin, 50 mg) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 3 hours of the reaction, the enzyme was filtered off and the excess of vinyl acetate was distilled out to obtain acetylated phosphatidylethanolamine. $H^1$-Nuclear Magnetic Resonance and Infrared spectral studies confirmed the presence of N-acetyl soup in acetylated phosphatidylethanolamine. The final yield of the product was 0.53 g

EXAMPLE 9

Pure phosphatidylethanolamine (0.5 g) isolated from egg yolk lecithin by silicic acid column chromatography was taken in 2.5 ml of vinyl acetate and lipase from *Mucor miehei* (10% of lecithin, 50 mg) was added to the contents. The reaction was carried out at 65–70° C. by stirring the contents magnetically. The acetylation reaction was monitored by thin layer chromatography using chloroform:methanol:water (65:25:4, v/v/v) as solvent system. The disappearance of pink color spot of phosphatidylethanolamine with ninhydrin spray indicated the completion of acetylation. After 3 hours of the reaction, the enzyme was filtered off and the excess vinyl acetate was distilled out to obtain acetylated phosphatidylethanolamine. $H^1$-Nuclear Magnetic Resonance and Infrared spectral studies confirmed the presence of N-acetyl group in acetylated phosphatidylethanolamine. The final yield of the product was 0.53 g The Main Advantages of the Present Invention are 1. The present invention is an enzymatic process for the preparation of acetylated phospholipids from vegetable lecithins such as soybean lecithin, rapeseed lecithin etc., animal lecithins like egg yolk lecithin, and pure phosphatidylethanolamine isolated from the above lecithins
2. The present invention uses vinyl acetate as acylating agent and also as a solvent.
3. The final product acetylated phospholipids can be. easily obtained by filtering off the lipase followed by removal of vinyl acetate by distillation.
4. The present invention selectively acetylates amino group of phosphatidylethanolamine without acetylation of hydroxyl group of phosphatidylinositol present in lecithin. This is possible only in the enzymatic acetylation using 1,3-specific lipase as described in the present invention. 1,3-Specific lipase does not allow the secondary hydroxyl group of phosphatidylinositol to participate in the reaction.

5. In the present invention the excess acylating reagent and the enzyme can be reused in the next batch of the reaction 6. The present invention provides an enzymatic method using lipase from *Mucor miehei* having 1,3-position specificity, which can be carried out under mild conditions compared to existing chemical methodologies and which is also an eco-friendly process.

We claim:

1. An enzymatic process for the preparation of an acetylated phospholipid from a lecithin or phosphatidylethanolamine, said process comprising acetylating the lecithin or phosphatidylethanolamine in the presence of an acetylating agent comprising vinyl acetate and a catalyst comprising lipase from *Mucor miehei* having 1,3-position specificity whereby to form an acetylated phospholipid, and separating the acetylated phospholipid.

2. A process as claimed in claim 1, wherein the lecithin is selected from the group consisting of vegetable lecithins and animal lecithins.

3. A process as claimed in claim 2, wherein the lecithin is a vegetable lecithin selected from the group consisting of soybean lecithin and rapeseed lecithin.

4. A process as claimed in claim 2, wherein the lecithin is an animal lecithin that comprises egg yolk lecithin.

5. A process as claimed in claim 1, wherein pure phosphatidylethanolamine isolated from the lecithin is acetylated with vinyl acetate in the presence of said catalyst and converted to the acetylated phospholipid.

6. A process as claimed in claim 1, wherein the acetylating agent selectively acetylates an amino group of phosphatidylethanolamine without acetylation of a hydroxyl group of phosphatidylinositol present in the lecithin.

7. A process as claimed in claim 1, wherein the process is a batch process and the acetylating agent and the catalyst are recycled after said acetylating step for subsequent use.

8. A process as claimed in claim 1, wherein the vinyl acetate is used in said acetylating step in the range of 0.5 to 5 times volume of vinyl acetate based on the weight of lecithin/phosphatidylethanolamine.

9. A process as claimed in claim 1, wherein the ratio of weight of the lecithin or phosphatidylethanolamine to the lipase is in the range of 20:1 to 10:1.

10. A process as claimed in claim 1, wherein the amount of the lipase comprises 5 to 10 weight percent based on lecithin/phosphatidylethanolamine.

11. A process as claimed in claim 1, wherein the acetylating is conducted at a temperature in the range of 65–75° C.

12. A process as claimed in claim 11, wherein the temperature is in the range of 70–75° C.

13. A process as claimed in claim 1, wherein the acetylating is conducted for a reaction time in a range of 3 to 11 hours.

14. A process as claimed in claim 13, wherein the reaction time is in the range of 3 to 8 hours.

* * * * *